United States Patent
Siess et al.

(10) Patent No.: US 12,076,544 B2
(45) Date of Patent: *Sep. 3, 2024

(54) BLOOD PUMP SYSTEM

(71) Applicant: Abiomed Europe GmbH, Aachen (DE)

(72) Inventors: Thorsten Siess, Aachen (DE); Frank Kirchhoff, Aachen (DE); Christoph Nix, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/212,207

(22) Filed: Jun. 21, 2023

(65) Prior Publication Data
US 2024/0024655 A1 Jan. 25, 2024

Related U.S. Application Data

(63) Continuation of application No. 16/077,097, filed as application No. PCT/EP2017/053033 on Feb. 10, 2017, now Pat. No. 11,724,091.

(30) Foreign Application Priority Data

Feb. 11, 2016 (EP) ..................................... 16155239

(51) Int. Cl.
*A61M 60/135* (2021.01)
*A61M 60/13* (2021.01)
(Continued)

(52) U.S. Cl.
CPC ........ *A61M 60/135* (2021.01); *A61M 60/148* (2021.01); *A61M 60/216* (2021.01);
(Continued)

(58) Field of Classification Search
CPC .. A61M 1/1008; A61M 1/1086; A61M 1/122; A61M 1/125; A61M 2205/3331
See application file for complete search history.

(56) References Cited

U.S. PATENT DOCUMENTS

| 5,964,694 A | 10/1999 | Siess et al. |
| 6,162,182 A | 12/2000 | Cole |

(Continued)

FOREIGN PATENT DOCUMENTS

| CN | 108601875 A | 9/2018 |
| JP | 2000511455 A | 9/2000 |

(Continued)

OTHER PUBLICATIONS

Office Action corresponding to Korean Patent Application No. 10-2018-7026096 dated Aug. 7, 2023 (8 pp.).

(Continued)

*Primary Examiner* — Jonathan T Kuo
*Assistant Examiner* — Vynn V Huh
(74) *Attorney, Agent, or Firm* — Botos Churchill IP Law LLP

(57) ABSTRACT

A blood pump system including a blood pump, an intravascular flow cannula, and a pressure sensor. The intravascular flow cannula is in flow communication with the blood pump and has a distal end portion distally from the blood pump and a proximal end portion closer to the blood pump. The intravascular flow cannula has at least one blood flow through opening at its distal end portion for blood to enter or exit the flow cannula. The blood flow through opening has a borderline surrounding the through opening. The pressure sensor is configured radially within the flow cannula and borders a proximal portion of the borderline.

9 Claims, 5 Drawing Sheets

(51) Int. Cl.
  *A61M 60/148* (2021.01)
  *A61M 60/216* (2021.01)
  *A61M 60/237* (2021.01)
  *A61M 60/422* (2021.01)
  *A61M 60/50* (2021.01)
  *A61M 60/816* (2021.01)
  *A61M 60/857* (2021.01)

(52) U.S. Cl.
  CPC ........ *A61M 60/422* (2021.01); *A61M 60/816* (2021.01); *A61M 60/857* (2021.01); *A61M 2205/3331* (2013.01)

(56) References Cited

U.S. PATENT DOCUMENTS

| | | | |
|---|---|---|---|
| 6,295,877 | B1 | 10/2001 | Aboul-Hosn et al. |
| 7,022,100 | B1 | 4/2006 | Aboul-Hosn et al. |
| 2003/0187322 | A1 | 10/2003 | Siess |
| 2004/0022640 | A1 | 2/2004 | Siess et al. |
| 2010/0268017 | A1 | 10/2010 | Siess |
| 2015/0141842 | A1 | 5/2015 | Spanier et al. |
| 2015/0290372 | A1 | 10/2015 | Muller et al. |
| 2016/0022890 | A1 | 1/2016 | Schwammenthal et al. |

FOREIGN PATENT DOCUMENTS

| | | |
|---|---|---|
| JP | 2003508161 A | 3/2003 |
| JP | 2007501644 A | 2/2007 |
| JP | 4159781 B2 | 10/2008 |
| JP | 2015514529 A | 5/2015 |
| WO | 0117581 A2 | 3/2001 |
| WO | 2011039091 A1 | 4/2011 |
| WO | 2013160407 A1 | 10/2013 |

OTHER PUBLICATIONS

First Office Action issued in corresponding Chinese Patent Application No. 201910758071.0 dated Jul. 6, 2021 (16 pp.).
ISR PCT/EP2017/053033 dated Apr. 24, 2017 (2 pages).
Office Action from corresponding Japanese Patent Application No. 2021-121203 dated Aug. 2, 2022, (10 pp.).
JP Office Action dated Oct. 31, 2023 for JP Appln. No. 2023-010875.
Office Action from corresponding Japanese Patent Application No. 2023-010875 dated Mar. 26, 2024 (8 pp.).

BLOOD PUMP SYSTEM

CROSS-REFERENCE TO RELATED APPLICATIONS

This application is a continuation of U.S. application Ser. No. 16/077,097, filed on Aug. 10, 2018, now U.S. patent Ser. No. 11,724,091, which application is a national phase entry under 35 U.S.C. § 371 of International Application No. PCT/EP2017/053033, filed Feb. 10, 2017, published in English, which claims the benefit of European Patent Application No. 16155239.3, filed Feb. 11, 2016, the contents of which are incorporated by reference herein in their entirety.

BACKGROUND OF THE INVENTION

This invention relates to a blood pump system comprising a blood pump and an intravascular flow cannula that is in flow communication with the blood pump and guides blood from a vessel towards the blood pump.

More specifically, the blood pump is an intravascular rotary blood pump which can be placed inside the vessel, such as the left ventricle or right ventricle or the aorta or any other blood vessel, as the case may be. The blood pump is driven by a motor which may be outside the patient's body or which may be placed inside the vessel along with the pump. In the former case, the pump is connected to the external motor via a flexible drive cable, whereas in the latter case the pump and the motor are combined to form an integral pumping device and receive energy preferably from outside the patient's body through a catheter. The latter structure is the preferred structure for the blood pump system of the present invention, but the present invention is not limited thereto.

When such blood pump systems are used for temporary heart support, they are introduced percutaneously into the femoral artery for example and guided through the body's vascular system in order to support or replace the pumping action in the heart, for example. During operation, the flow cannula protrudes through a cardiac valve opening to enable blood to be pumped through the cardiac valve by means of the pump. Furthermore, the blood pump system is equipped with pressure sensors externally on the housing of the blood pump and externally on the flow cannula in order to establish the inlet pressure and the outlet pressure. Data regarding the inlet and outlet pressures, together with the power consumption of the electrical motor of the blood pump system, form a set of relevant information for the function and delivery rate of the blood pump system. In addition, the measured pressures enable inferences to be drawn about the positioning of the blood pump in the vascular system. Moreover, a comparison of the differential pressure with the current power consumption of the motor enables local states as well as cavitation and sucking to be ascertained.

WO 2013/160407 A1 proposes to provide the blood pump system with two or more than two pressure sensors. For example, pressure sensors may be provided externally on the blood pump system at the proximal end of the blood pump and/or at the distal end of the flow cannula. An additional pressure sensor may be provided within the flow cannula for determining when the flow cannula is being sucked against a heart chamber wall. It is stressed in WO 2013/160407 A1 that, in addition to the pressure sensor inside the flow cannula, it is also important to have a pressure sensor externally on the flow cannula in proximity of its blood flow through openings in order to measure the physiological blood pressure there and particularly addresses preferential arrangements for the external pressure sensor on the flow cannula for measuring the physiological pressure in the patient's ventricle.

BRIEF SUMMARY OF THE INVENTION

The object of the present invention is to further improve known blood pump systems in respect of the arrangement of pressure sensors.

Accordingly, the blood pump system of the present invention comprises a blood pump and an intravascular flow cannula in flow communication with the blood pump and has a pressure sensor arranged at the flow cannula's distal end portion inside the flow cannula in an area of the blood flow through opening or bordering the area of the blood flow through opening. The flow cannula's distal end portion is the end portion which is further away, i.e. distal, from the blood pump, and the blood flow through opening at the flow cannula's distal end serves the purpose for blood to enter the flow cannula on its way to the pump or, when the pump is driven in reverse direction, to exit the flow cannula.

It is important that the pressure sensor is arranged within the flow cannula. In this way, when the flow cannula is being sucked against a heart chamber wall or the flow cannula is otherwise displaced, the pressure sensor cannot be covered by the heart chamber wall or blocked in any other way. Therefore, an indication by the pressure sensor that the pressure is about zero or the rhythmical pressure difference of the heart beat quickly decreases is a clear signal that the flow cannula is being sucked against the heart chamber wall, for example. In other words, the pressure sensor arranged inside the flow cannula can be used, in particular, to serve as a wall suction indicator.

However, because of its specific arrangement in the area of the flow cannula's blood flow through opening or bordering the area of the blood flow through opening, the same pressure sensor can be used to serve a second purpose, namely to measure or at least approximately measure the pressure external of the flow cannula, such as the pressure inside the left or right ventricle of the heart, as the case may be, because the blood pressure in the area of the blood flow through opening substantially coincides with the blood pressure outside the flow cannula. Accordingly, the proposed special location of the pressure sensor makes it possible to do without a separate external pressure sensor on the outside of the flow cannula. In particular, according to a preferred embodiment of the invention, the blood pump system may be adapted to determine a differential pressure from a first pressure value provided by the pressure sensor arranged within the distal end portion of flow cannula and a second pressure value provided by a second pressure sensor arranged outside the blood pump, e.g. on the blood pump housing.

BRIEF DESCRIPTION OF THE DRAWINGS

Hereinafter the invention will be explained by way of example with reference to the accompanying drawings. Therein are shown.

DETAILED DESCRIPTION

Figure 1:
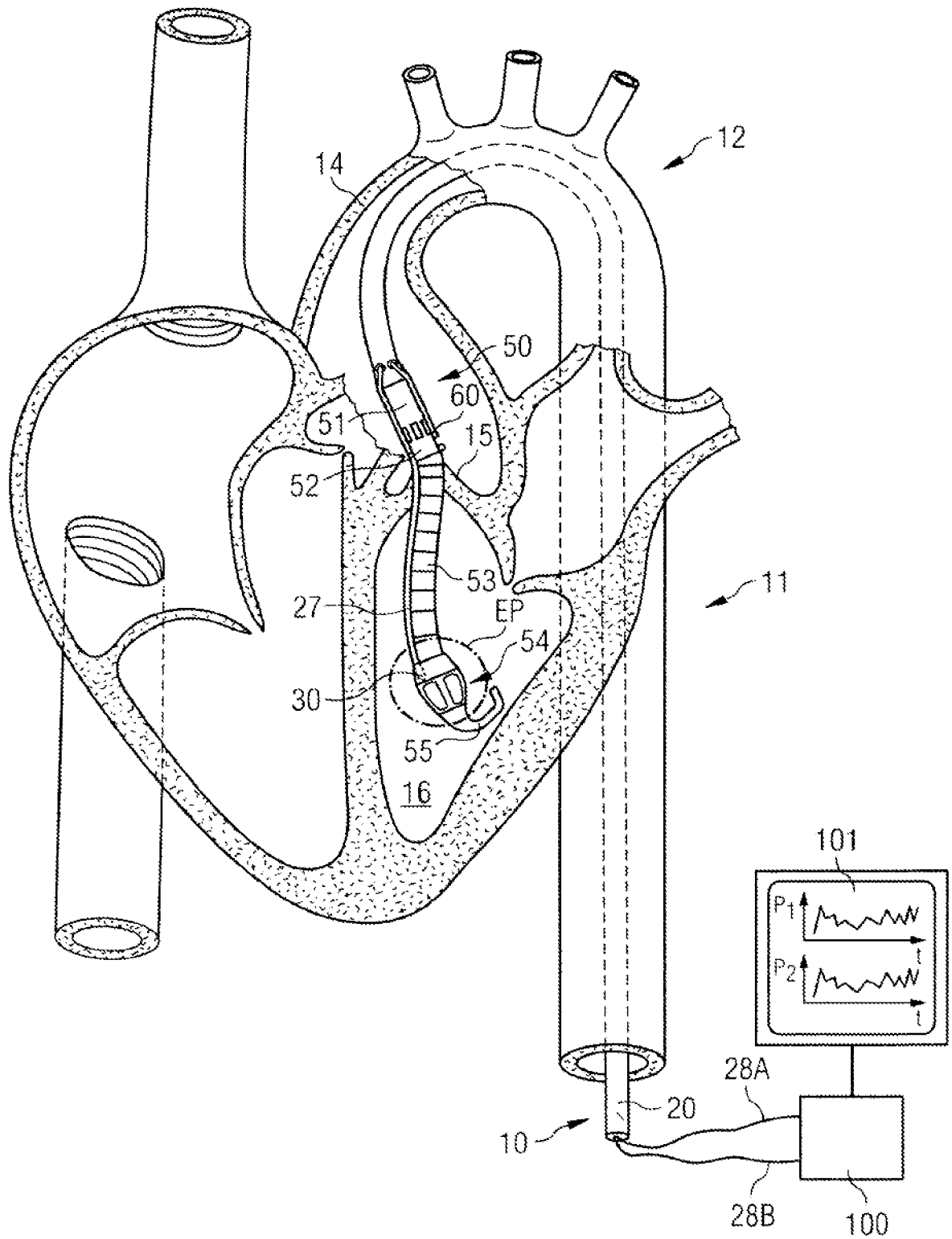
FIG. 1 a blood pump system with the blood pump and flow cannula laid through the aorta and extending through the aortic valve into the left ventricle (16), FIG. 2A to 2D various options for placing the pressure sensor within the flow cannula, and FIGS. 3A and 3B two variants of frame structures defining an inflow cage of the flow cannula.

FIG. 1 shows a blood pump system having a catheter 10 which, in this example, is introduced into the descending aorta 11 retrograde. The descending aorta 11 is part of the aorta 12 which first ascents from the heart and then descents and has the aortic arch 14. At the beginning of the aorta 12 there is located the aortic valve 15 which connects the left ventricle 16 to the aorta 12 and to which the intravascular blood pump system extends. The blood pump system comprises in addition to the catheter 10 a rotary pump 50 fastened at the distal end of a catheter hose 20 and having a motor section 51 and a pump section 52 disposed at an axial distance from the motor section 51, as well as a flow cannula 53 protruding in the distal direction from the inflow end of the pump section 52. The flow cannula 53 has a blood flow through opening 54 at its distal end portion EP forming a suction inlet or, if the pump 50 is driven in reverse direction, a blood flow outlet. Distally of the through opening 54 there is provided a soft-flexible tip 55, which can be configured for example as a "pigtail" or in a J-shape. Through the catheter hose 20 there extend different lines and devices which are important for operating the pumping device 50. Of these, FIG. 1 only shows two optical fibers 28A, 28B which are attached at the proximal end to an evaluation device 100. These optical fibers 28A, 28B are respectively part of optical pressure sensors who's sensor heads 30 and 60 are located externally on the housing of the pump section 52, on the one hand, and internally in the distal end portion EP of the flow cannula 53, on the other hand. The pressure transmitted by the sensor head 30 and 60 is converted into electrical signals in the evaluation device 100 and displayed e.g. on a display screen 101.

As already stated, the invention is not limited to a rotary pump with integrated motor section 51. Instead, the motor for driving the pump may be provided externally of the patient and a flexible drive cable may connect the pump with the external motor.

The measurement of both the aortic pressure by means of the sensor head 60 and the ventricular pressure by means of the sensor head 30 makes possible, in addition to the actual pressure signal, e.g. a contractility measurement by which the recovery of the heart is measured, as well as the establishment of the pressure difference which is used for computing the flow of the pumping device 50. The principle of electro-optical pressure measurements as well as the structure and arrangements of the optical fibers is explained in more detail in WO 2013/160407 A1, the respective disclosure being incorporated herein by reference. The present invention differs from that disclosure only in that the pressure sensor 30 is placed at a specific position inside the flow cannula 53, rather than on the flow cannula's external surface, as will be explained hereinafter.

Figure 2A:
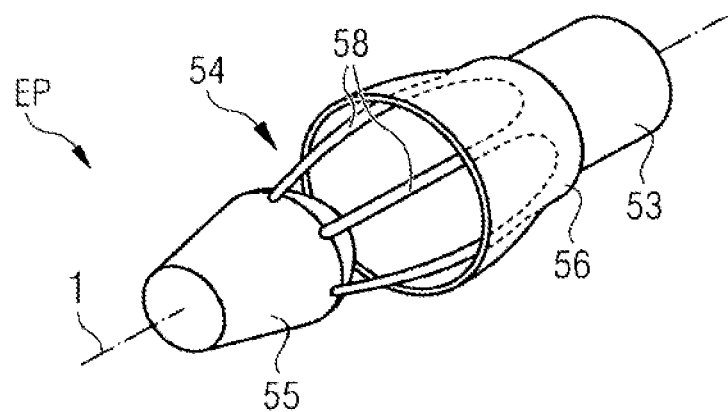
Figure 2B:
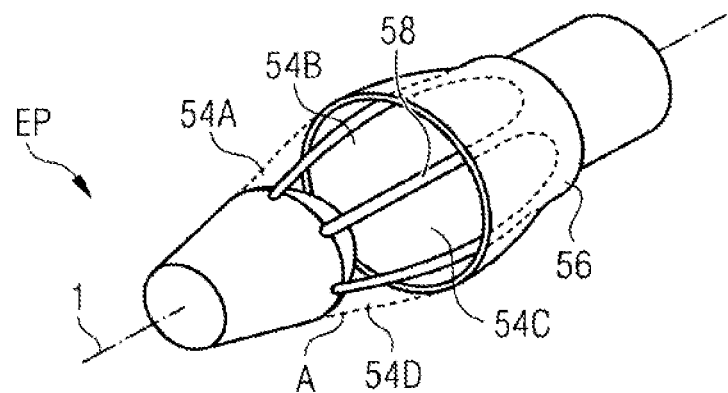

FIG. 2A shows the distal end portion EP of the flow cannula 53 in more detail according to a preferred embodiment. With respect to its general longitudinal axis 1, the end portion EP comprises a radial blood flow through opening 54 for blood to enter or, as the case may be, exit the flow cannula 53. In the area of the blood flow through opening 54, a frame structure comprising a plurality of struts 58 is provided so as to form a cage which serves two purposes. First, the struts 58 connect the flow conducting part of the flow cannula 53 with the soft-flexible tip 55. Second, the cage-forming frame structure prevents the heart chamber wall from being sucked into and blocking the flow cannula 53. Accordingly, the struts 58 may generally extend axially, but they may likewise extend helically, cross each other and/or have interconnections. As shown in FIG. 2B, the struts 58 divide the blood flow through opening 54 in separate blood flow openings 54A to 54D. The dashed lines in the area of the blood flow through opening 54A and 54D mark the outer limits of the flow cannula 53 in the area A of the blood flow inlet 54.

Figure 2C:
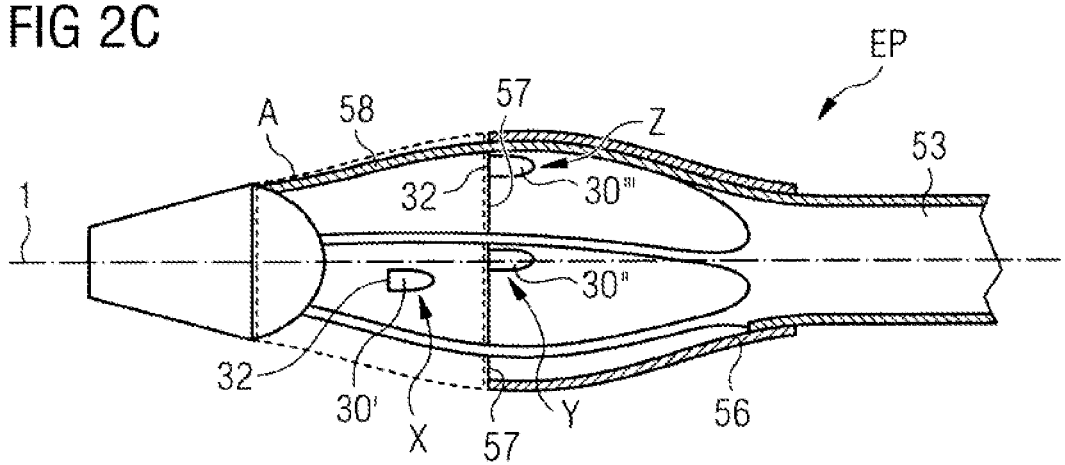

FIG. 2C is a cross-sectional view through the end portion EP. The area A surrounded by a dashed line indicates the level of the blood flow through opening 54 or openings 54A to 54D, respectively, with respect to the flow cannula's longitudinal axis 1. This is the area where the pressure sensor 30 may be positioned inside the flow cannula. For instance, the pressure sensor may be placed at a position X, as shown in FIG. 2C and exemplified by pressure sensor 30' which is only schematically shown. In any case, the pressure sensitive surface 32 of the pressure sensor 30' should be oriented perpendicularly to the longitudinal axis 1 for reasons explained in more detail in WO 2013/160407 A1, namely to increase measurement accuracy so as to enable high-frequency physiological signals up to 250 Hz to be derived from the signal data.

Rather than placing the pressure sensor 30 somewhere in the area A of the blood flow through opening 54, it may border area level A. Preferably, it is positioned at a proximal border thereof, as exemplified in FIG. 2C by pressure sensors 30" and 30'''. Again, pressure sensors 30" and 30''' located at positions Y and Z are only schematically shown and their pressure sensitive surfaces 32 are likewise oriented perpendicularly to the longitudinal axis 1. That is, the blood flow through opening 54 or each of the at least one blood flow through openings 54A to 54D, respectively, have a borderline surrounding the through-opening 54 or 54A to 54D, respectively, and said borderline has a proximal portion which, in the embodiment shown in FIG. 2, is formed by the end face 57 of a funnel structure 56 which forms part of the flow cannula 53. The funnel structure may be formed from a thin film, in particular a thin polymer film. It is preferable to arrange the pressure sensor 30 exactly at the level of the proximal portion 57 of the borderline surrounding the through opening 54 or through openings 54A to 54D, preferably with its pressure sensitive surface, as is shown in FIG. 2C by pressure sensors 30" and 30'''. Thereby, during normal pump operation, the global pressure within the ventricular cavity can be sensed with minimal to no interference with the pump flow. In addition, should suction be present, then the sensor in this preferred position would also be able to detect the negative pressure due to suction, which is a local phenomenon at the inlet. More preferably, the pressure sensor is arranged on and preferably fixed to the frame structure, e.g. to a strut 58. The position can be tangentially from the strut 58, as shown by pressure sensor 30" in FIG. 2C, or, more preferably, on a radial inner side of the frame structure, as shown by pressure sensor 30''' in FIG. 2C.

Figure 2D:
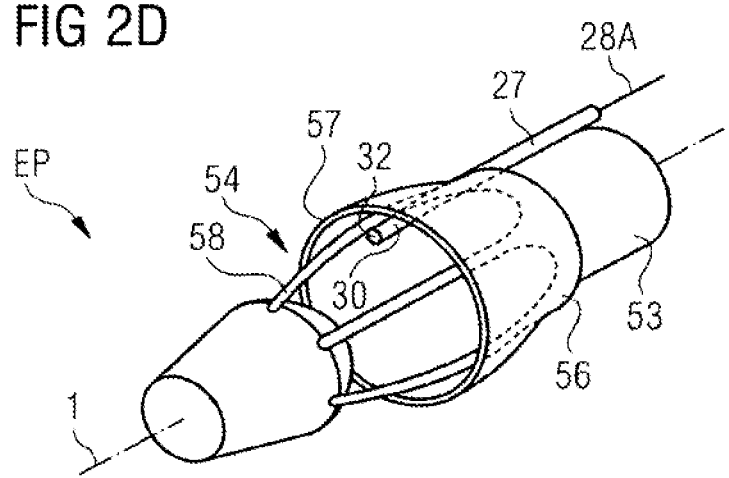

FIG. 2D shows a specific example of how the pressure sensor 30 may be placed inside the flow cannula 53, corresponding to the position Z of pressure sensor 30''' in FIG. 2C. Accordingly, the pressure sensitive surface 32 of pressure sensor 30 borders the level of the blood flow through opening 54 exactly at the proximal portion 57 of the borderline surrounding the through opening 54, which proximal portion 57 is defined by the end face of the funnel structure 56 surrounding the frame structure of the end portion EP. As can be seen, the optical fiber 28A, or plurality of fibers, is protected within a separate lumen 27 within which it is freely movable. The lumen 27 may consist of a polymer, in particular polyurethane, or preferably of nitinol or another shape-memory alloy and is laid along the flexible flow cannula 53 externally. Lumen 27 enters the flow cannula 53 through the funnel structure 56, and the distal end of the optical fiber 28A with the pressure sensor 30 is fixed on a radial inner side of a strut 58.

While the invention has been described with respect to an end portion EP having an enlarged cross section as compared to the rest of the flow cannula 53, the invention is not limited in this respect. However, an enlarged cross section and, in particular, the funnel shape structure 56 funnelling from distal to proximal is advantageous because the pressure drop in the blood flow along the axis 1 of the flow cannula is less rapid within the funnel shape as compared to the pressure drop inside the non-funnelling rest of the flow cannula 53. Therefore, accurate placement of the pressure sensor 30 exactly at the proximal portion 57 of the borderline surrounding the through-opening is less critical in a funneling flow cannula and misplacement of the pressure sensor 30 minimally further axially inside the flow cannula 53 will have less influence as compared to a non-funneling structure. At least the struts 58 of the frame structure are made from a shape-memory alloy, such as nitinol, or a shape memory polymer and the funnel structure 56 surrounding the frame structure is made from a flexible material so that, upon insertion of the flow cannula 53 through the patient's vascular system, the frame structure along with the funnel structure 56 has substantially the same diameter as the rest of the flow cannula 53. The expanded configuration with enlarged cross section will be assumed after placement of the device when the frame structure reaches body temperature.

Figure 3A:
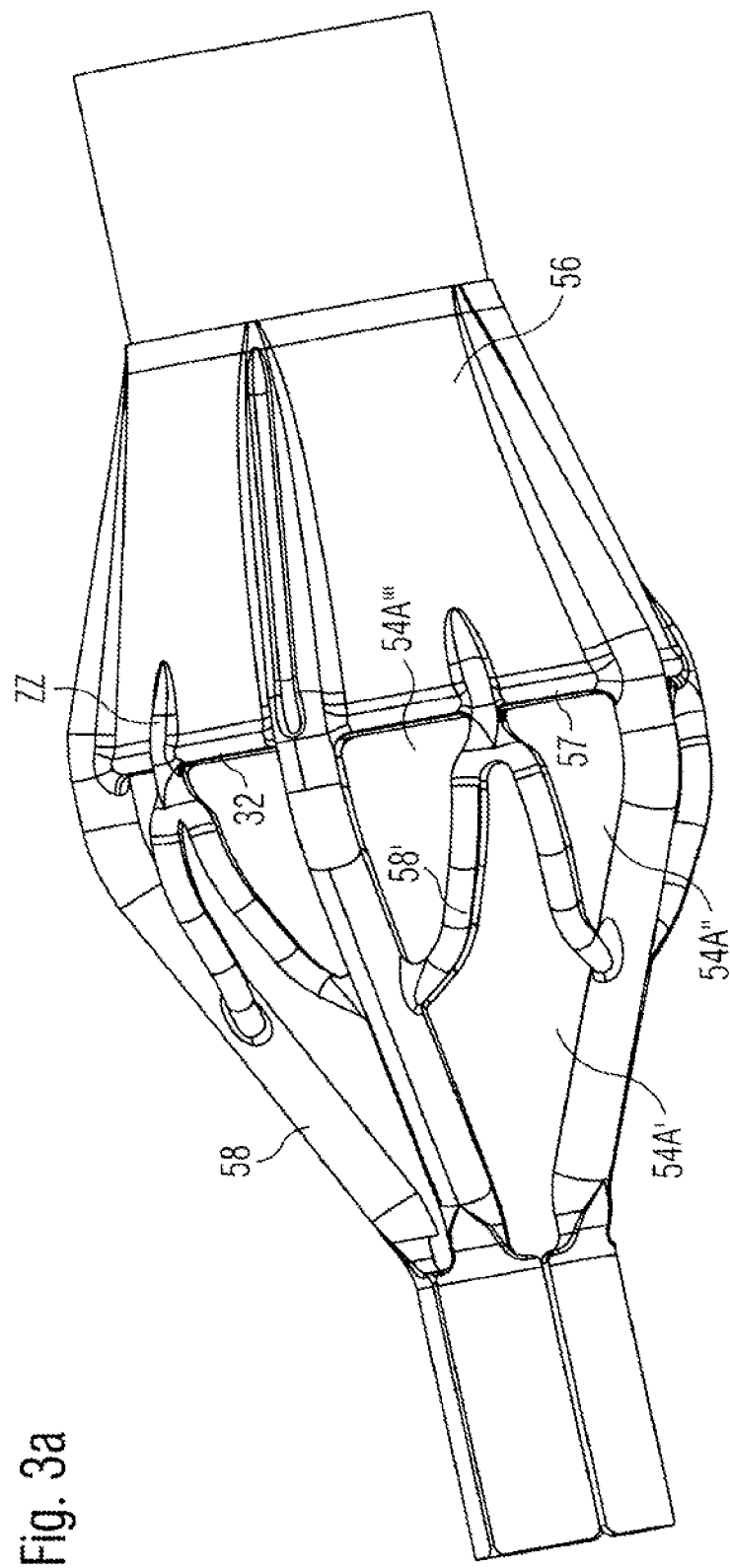
Figure 3B:
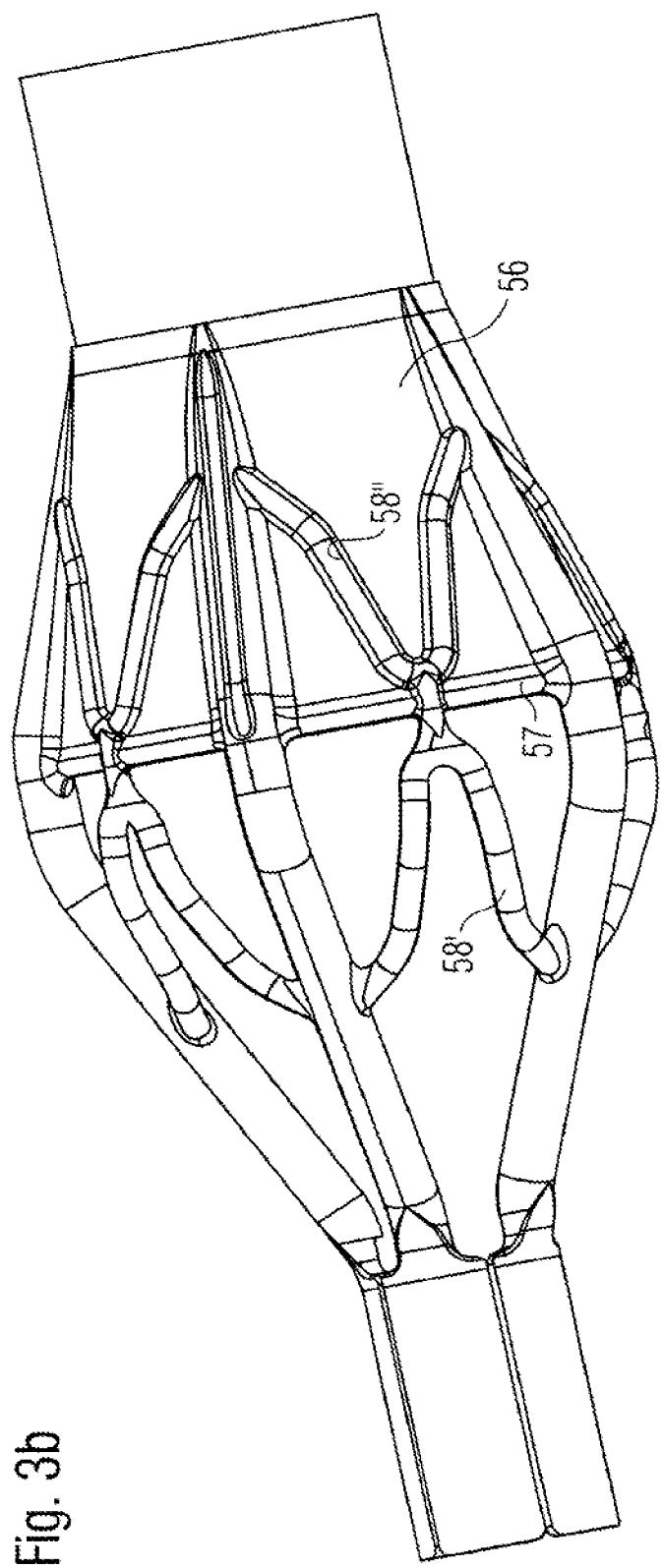

FIGS. 3a and 3b illustrate alternative versions of an expandable frame structure defining the inflow cage. In FIG. 3a, interconnecting struts 58 are provided between the main struts providing a structure which further divides the inlet/outlet openings 54A-D into smaller openings 54A'-A'''. Thereby, the ingestion of highly flexible structures like the apparatus of a valve (mitral valve: leaflets, cordae, papillary structure) can be avoided. Here, the preferred sensor position, marked ZZ in FIG. 3c, would be radially inside the interconnecting struts assembly 58' at a junction of the interconnecting struts 58' and the end face 57 of the funnel structure 56, e.g. the rim of the thin polymer film.

In FIG. 3b the same interconnecting strut assembly 58' is present, and in addition it is likewise provided, e.g. mirrored (58''), on the side of the flexible funnel structure 56. Thereby, local inward bending of the funnel structure 56 can be avoided, which may otherwise occur during normal flow condition due to a local pressure drop when the flow enters the inlet, or during a suction event, when sincere negative pressures may be present. The inflow end face 57 of the funnel structure 56 can further be structurally improved by locally increasing the thickness of the funnel structure. A radially stiffer funnel structure 56 is particularly advantageous in order to release from cardiac structures after a sucking event.

The invention claimed is:

1. A blood pump system comprising:
   an intravascular flow cannula that is in fluid communication with a blood pump and has a distal end portion and a proximal end portion, wherein the distal end portion of the intravascular flow cannula comprises at least one blood flow through opening for blood to enter or exit the intravascular flow cannula, wherein the at least one blood flow through opening has a borderline surrounding the at least one blood flow through opening and the borderline defines a proximal portion of the at least one blood flow through opening; and
   a pressure sensor, wherein a portion of the pressure sensor is placed inside the distal end portion of the intravascular flow cannula, wherein the portion of the pressure sensor includes a pressure sensitive surface that borders the proximal portion of the at least one blood flow through opening defined by the borderline such that the pressure sensor is configured to (a) measure a pressure external to the distal end portion of the intravascular flow cannula, and (b) detect a negative pressure due to suction of the distal end portion of the intravascular flow cannula against patient tissue, based on values sensed by the pressure sensor.

2. The blood pump system of claim 1, wherein the distal end portion of the intravascular flow cannula comprises a frame structure that forms a cage.

3. The blood pump system of claim 2, wherein the frame structure comprises a plurality of struts that form the cage and the borderline surrounds the cage.

4. The blood pump system of claim 2, wherein the distal portion of the cage has a funnel structure formed thereover, wherein the funnel structure extends to the flow cannula and the distal end of the funnel structure defines the borderline.

5. The blood pump system of claim 3, wherein the portion of the pressure sensor is arranged on and fixed to one of the plurality of struts of the frame structure.

6. The blood pump system of claim 1, further comprising the blood pump.

7. The blood pump system of claim 6, wherein the blood pump is coupled to the proximal end portion of the intravascular flow cannula.

8. The blood pump system of claim 7, further comprising a second pressure sensor placed outside the blood pump, wherein the blood pump system is configured to determine a differential pressure from a first pressure value provided by the pressure sensor placed inside the distal end portion of the intravascular flow cannula and a second pressure value provided by the second pressure sensor placed outside the blood pump.

9. The blood pump system of claim 8, wherein the blood pump comprises a blood pump housing and the second pressure sensor is placed on the blood pump housing.

* * * * *